United States Patent [19]

Pfeiffer

[11] 4,456,594

[45] Jun. 26, 1984

[54] N-CARBOXYALKYLPROLINE-CONTAINING TRIPEPTIDES

[75] Inventor: Francis R. Pfeiffer, Cinnaminson, N.J.

[73] Assignee: SmithKline Beckman Corporation, Philadelphia, Pa.

[21] Appl. No.: 435,860

[22] Filed: Oct. 21, 1982

Related U.S. Application Data

[63] Continuation-in-part of Ser. No. 318,721, Nov. 6, 1981, abandoned.

[51] Int. Cl.³ .................... A61K 37/00; C07C 103/52
[52] U.S. Cl. .......................... 424/177; 260/112.5 R; 424/274; 548/518
[58] Field of Search ............... 548/518; 424/177, 274; 260/112.5 R

[56] References Cited

U.S. PATENT DOCUMENTS 4,299,769 11/1981 McEvoy et al. .................... 548/518
4,342,689 8/1982 McEvoy et al. .................... 548/518

OTHER PUBLICATIONS

Chem. Abstr. vol. 53, 21693h.

*Primary Examiner*—Delbert R. Phillips
*Attorney, Agent, or Firm*—William H. Edgerton; Richard D. Foggio; Alan D. Lourie

[57] ABSTRACT

Certain N-carboxyalkyl prolyl-containing tripeptides have been prepared and found to improve kidney function. A species of the group of new compounds is N-(2-carboxyethyl)-L-prolyl-L-alanyl-L-proline which has diuretic activity and increases renal blood flow. The compounds are prepared by chemical reactions which couple an amino acid with a dipeptide.

12 Claims, No Drawings

N-CARBOXYALKYLPROLINE-CONTAINING TRIPEPTIDES

This application is a continuation-in-part of U.S. patent application Ser. No. 318,721 filed Nov. 6, 1981, now abandoned.

This invention comprises a group of new chemical compounds which have biological activity whose structures have a tripeptide chain with two prolyl end units separated by a spacer unit. One of the prolyl units has an essential N-(acid functionalized alkyl)-substituent. The biological activity of these compounds is to increase renal blood flow and induce diuretic activity. As such, the compounds are useful for treating hypertension or for improving renal function.

BACKGROUND OF THE INVENTION

K. T. Poroshin et al., Chemical Abstracts, 53 21693h, described the use of carbobenzoxy-L-prolylglycyl-L-proline as an intermediate to prepare L-prolylglycyl-L-proline, however, this reference described neither the essential N-carboxyalkyl substituent nor the critical mid-unit both of which characterize the structures of these new compounds. Poroshin, also, described no biological activity for any of the compounds he prepared. The compounds of this invention, therefore, differ from those in the prior art by two structural parameters.

EPO application No. 12,401 describes certain carboxyalkyl dipeptides which are angiotensin converting enzyme inhibitors. The EPO compounds differ from those of the present invention in mechanism of action as well as in chemical structure. The N-carboxyalkyl substituents are not substituted on the prolyl unit of the EPO dipeptides.

DESCRIPTION OF THE INVENTION

As stated above, the group of new chemical compounds of this invention is characterized by having tripeptide structures which are prolyl-spacer-prolines with an acid functionalized alkyl substituent at the free N-member of the prolyl ring. The structures, therefore, contain two acid groups, one of which is amphoteric.

Exemplary of the compounds of this invention are those represented by formula I:

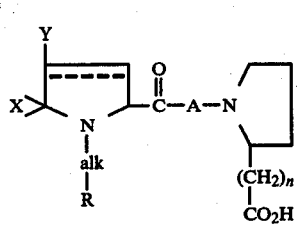

in which:

R is an acid group such as carboxy ($-CO_2H$), sulfo ($-SO_2OH$) or phosphono ($-P(O)(OH)_2$);

alk is a straight or branched alkylene chain of 1-5 carbons which is not an ethylidene ($=CH-CH_3$);

X is O or H,H;

Y is H or, when X is H,H, $-OH$;

is an optional carbon-carbon bond only when X and Y are H,H or H, respectively;

n is an integer of from 0-3, inclusive; and

A is a spacer amino acid unit in combined peptide form such as,

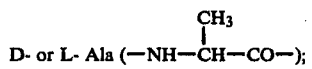

D- or L- Ala ($-NH-CH(CH_3)-CO-$);

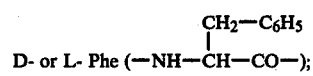

D- or L- Phe ($-NH-CH(CH_2-C_6H_5)-CO-$);

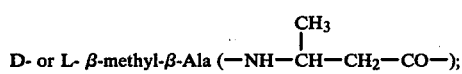

D- or L- β-methyl-β-Ala ($-NH-CH(CH_3)-CH_2-CO-$);

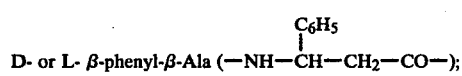

D- or L- β-phenyl-β-Ala ($-NH-CH(C_6H_5)-CH_2-CO-$);

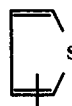

D- or L- β-thienyl-Gly ($-NH-CH-CO-$);

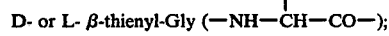

D- or L- phenyl-Gly ($-NH-CH(C_6H_5)-CO-$);

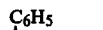

D- or L- β-Ala ($-NH-CH_2-CH_2-CO-$);
γ-aminobutyric acid ($-NH-CH_2-CH_2-CH_2-CO-$);

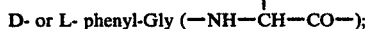

D- or L- 2-aminobutyric acid ($-NH-CH(C_2H_5)-CO-$);

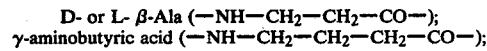

D- or L- nor-Val ($-NH-CH(C_3H_7)-CO-$);

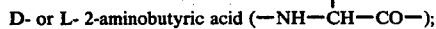

D- or L- nor-Leu ($-NH-CH(C_4H_9)-CO-$);

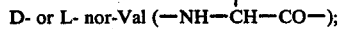

3-amino-3-methylbutyric acid ($-NH-C(CH_3)_2-CH_2-CO-$); and

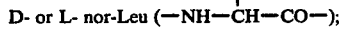

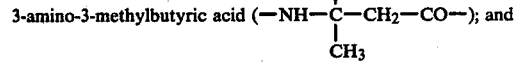

2-methyl-Ala ($-NH-C(CH_3)_2-CO$);

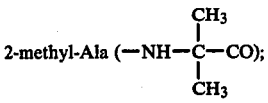

or N-methyl derivatives of said spacer units.

A subgeneric group of this invention comprises those compounds of formula I in which A is a substituted or unsubstituted β-Ala. A useful species is that of formula I in which R is carboxy, alk is methylene, X is H,H, Y is H, n is O and A is β-Ala. Preferably, the configuration of the amino acid units of each of the above groups of compounds will be L. The species, N-carboxymethyl-L-prolyl-β-alanyl-L-proline sulfate, is an advantageous compound of this invention.

In the definition of the compounds of formula I above, the end unit is which X is O will be recognized as a pyroglutamyl ring, the unit in which Y is OH will be recognized as a hydroxy prolyl ring and the unit in which a double bond is present will be recognized as a dehydroprolyl ring. All these are, essentially, prolyl derivatives.

In the renal anesthetized dog screening protocol described hereafter, N-carboxymethyl-L-prolyl-L-lysyl-L-proline, N-carboxymethyl-prolyl-glycyl-L-proline and N-(1-carboxyethyl)-L-prolyl-β-alanyl-L-proline were inactive as renal vasodilators in the primary test period of the screening protocol. This illustrates the critical nature of the spacer unit as well as of the N-alkyl substituent on the prolyl end unit.

These compounds include the various pharmaceutically acceptable salt forms of the invention, such as those formed with nontoxic acids at the basic N-member of the N-carboxyallkylprolyl fragment or those formed having pharmaceutically acceptable cations associated with the anionic acid groups. The former include the sulfate, hydrochloride, phosphate, hydrobromide, ethanedisulfonate or methane-sulfonate. The latter include the sodium, potassium, calcium and similar salts with strong bases. The alkali metal salts are most useful as intermediates rather than end products although they may be used either way.

The salts are formed by reacting the compounds of formula I in a suitable solvent with an appropriate acid or base, using reaction conditions which will be readily apparent to those skilled in the art. Usually, an excess of the inorganic acid or base is reacted with the compound of this invention dissolved in water or in an appropriate organic solvent, such as aqueous ethanol. The compounds of this invention, often, form solvates, such as hydrates or lower alcoholates.

The acid addition salts, such as the sulfate, are most useful forms of the compounds of this invention as are the parent tripeptides.

Further, the diacids of formula I may be used in prodrug forms such as an amide, a lower alkyl ester derivative of from 1–5 carbons in each of said alkyl groups or a benzyl ester.

These compounds are prepared by a synthetic sequence in which the key reaction is as follows:

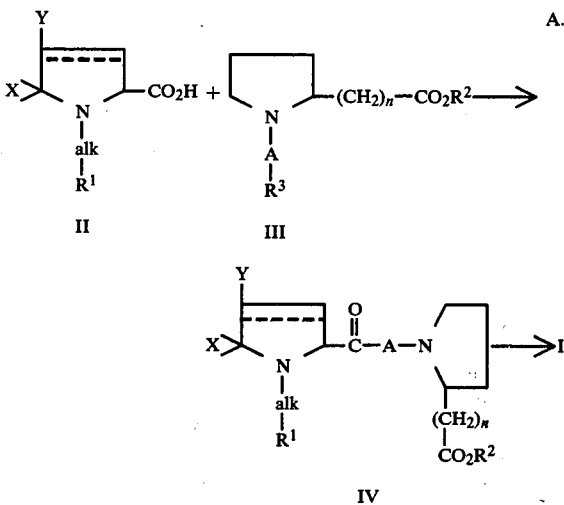

In sequence A, X, Y, or n are as defined above. $R^1$ is a protected form of carboxy, sulfo or phosphono, such as a benzyl ester or lower alkyl ester thereof, $R^2$ is a carboxy protective group, such as benzyl or lower alkyl, and $R^3$ is the amino (—NH$_2$) or N-methylamino

of the spacer amino acid unit.

An N-(acid functionalized alkyl) proline (II) in a form which will protect the side chain acid group is reacted with a proline-containing dipeptide with its terminal acid group protected (III) to give the products of this invention in the form of the protected dicarboxylic acids (IV). In the formation of the amide bond during the reaction between the amino acid and the dipeptide starting materials, any reaction conditions of a peptide coupling reaction are used. Especially useful is the reaction of the amino acid unit (II) with the dipeptide (III) in the presence of an acylation promoter such as a carbodiimide, for example, dicyclohexylcarbodiimide. The reaction is carried out in an organic solvent, for example, tetrahydrofuran, dimethylacetamide or dimethylformamide using moderate temperatures until the reaction is complete. Room temperature for from 1–18 hours is used in many cases.

Other coupling methods used involve isoxazolium derivatives, 1-ethoxycarbonyl-2-ethoxy-1,2-dihydroquinoline, a phosphonium derivative, the N-carboxy anhydride derivatives or a N-hydroxysuccinimide ester derivative. More specific details of various coupling methods are described in "Peptide Synthesis", Bodanszky, Wiley (1976) Chapter Five.

The protecting ester groups are, then, removed by standard reactions which do not effect the amide bonds, such as by using catalytic hydrogenation for O-benzyl groups or by using controlled alkali hydrolysis, such as by using barium hydroxide.

The compounds are, also, prepared utilizing solid phase technology commonly used in preparing peptides.

The compounds of this invention have pharmacodynamic activity and, acting on the kidney, are useful pharmaceutical compounds. More specifically, they increase renal blood flow or decrease renal vascular resistance. Their effect in improving kidney function, often, appears to be cumulative. They, also, have diuretic activity. These compounds, therefore, are relatively long acting antihypertensive or kidney function improving agents. Surprisingly, the compounds of this invention have activity after either oral or parenteral administration.

The biological activity of the compounds of formula I was demonstrated by administering the compounds by infusion to anesthetized dogs measuring the mean arterial blood pressure, renal blood flow, renal vascular resistance and heart rate in the test procedure explained in detail in U.S. Pat. No. 4,197,297. Generally speaking, the compounds gave a decreased renal vascular resistance and increased renal blood flow at doses ranging from ⅓ to 1/100 of that for dopamine in this test procedure. Representative specific results are included in the examples.

The compounds, alternatively, demonstrate biological activity in spontaneously hypertensive rats (SHR). In this test, male, Okamato-Aoki strain, spontaneously hypertensive rats, aged 16–19 weeks, are fasted, then, the following afternoon, the first dose of test compound is administered, along with a 25 ml/kg p.o. load of normal saline. The animals are, then, placed in metabolism cages and urine collected for three hours for analysis. Indirect systolic blood pressure and heart rate are measured by a tail-cuff. An identical second dose of test compound is administered. After two hours, blood pressure and heart rate are again tested. The test compound is usually administered p.o. or i.p. in saline with 0.02% ascorbic acid. In this test, representative drugs of this invention demonstrated diuretic activity.

For example, (N-carboxymethyl)-L-prolyl-β-alanyl-L-proline hemisulfate i.p. demonstrated a significant increase in Na⊕, K⊕ or urine excretion at 25 and 50 mg/kg i.p. It had a RVR-ED$_{15}$ of 12 μg/kg in the anesthetized renal dog protocol (dopamine was 3.5 μg/kg). It did not have angiotensin coverting enzyme inhibiting activity at 10 times its renally effective dose. This species, also, did not stimulate or antagonize the dopamine-sensitive adenylate cyclase system in vitro, nor was it active in the toad bladder anti-ADH assay. The compound demonstrated a weak bradycardic effect.

The new chemical compounds, described above, are incorporated into dosage unit forms such as capsules, tablets or injectable preparations which are useful for improving renal function, treating high blood pressure or inducing diuresis. The pharmaceutical carrier for the dosage units employed may be, for example, either a solid or liquid. Exemplary of solid carriers are lactose, terra alba, sucrose, talc, gelatin, agar, pectin, acacia, magnesium stearate or stearic acid. Exemplary of liquid carriers are syrup, peanut oil, olive oil or water. Similarly, the carrier or diluent may include any time delay material well known to the art, such as glyceryl monostearate of glyceryl distearate alone or with a wax. Such sustained release products as well as derivatives which may be gradually metabolized to the active parent can be employed to prolong the unique biological activity of the compounds of this invention if considered necessary.

A wide variety of pharmaceutical forms can be employed. Thus, if a solid carrier for oral administration is used the preparation can be tableted, placed in a hard gelatin capsule in powder, suppositories regular or sustained release pellet form, in the form of a troche or lozenge. The amount of solid carrier will vary widely but, preferably, will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary for tablet forms, or mixing, filling, and dissolving the ingredients, as appropriate to give the desired oral or parenteral end products.

The doses of the present compounds in the pharmaceutical dosage unit will be an effective, nontoxic quantity selected from the range of 10-350 mg of active tripeptide, preferably 50-200 mg. The selected dose is administered to a patient in need of treatment for the one of the noted clinical conditions from 1-5 times daily, orally, by injection or by infusion. Parenteral administration which uses a lower dose chosen from the dose range, individually or combined, is preferred, however, oral administration, from 1-5 times a day at higher doses, is also used when convenient for the patient.

One skilled in the art will recognize that the compounds of this invention may exist in various configurations such as optical isomers or mixtures thereof. Isomeric compounds are easily prepared by substituting the amino acid of a selected configuration into the chemical reactions of the examples which illustrate this invention or by chromatographic separation of an isomeric mixture by high pressure liquid chromatography.

The following examples are intended to teach the preparation and use of the new compounds of this invention but not to limit its scope. All temperatures are expressed in degree Centigrade.

EXAMPLE 1

A mixture of 6.0 g (0.025 m) of the benzyl ester of L-proline, 4.7 g (0.025 m) of N-tert.-butoxycarbonyl-L-alanine, 6.75 g (0.05 m) of 1-hydroxybenzotriazole, 3.2 ml (2.82 g, 0.025 m) of N-ethylmorpholine and 65 ml of dry tetrahydrofuran was cooled, filtered and added to a mixture of 5.15 g (0.025 m) of dicyclohexylcarbodiimide and 10 ml of tetrahydrofuran. The mixture was stirred at 0° for 30 minutes, then, at 25° for 18 hours. The reaction mixture was filtered. The filtrate was evaporated to give a residue which was dissolved in ethyl acetate. The solution was washed with 1 to 10% acetic acid, water, 5% sodium bicarbonate solution and brine, then, dried over anhydrous magnesium sulfate and concentrated to leave 9.8 g of crude N-tert.-butoxycarbonyl-L-alanyl-L-proline, benzyl ester (the t-boc).

A mixture of 2 g of the t-boc, 3.0 g of trifluoroacetic acid and 15 ml of dry methylene chloride was allowed to react at room temperature for 2 hours, then, evaporated under reduced pressure to give the crude trifluoroacetate salt. The salt was dissolved in ether and acidified with ethereal hydrogen chloride to give 1.15 g white solid L-alanyl-L-proline, benzyl ester hydrochloride, m.p. 162°-164°.

About 500 mg of 10% palladium-on-charcoal, wet with water, was added to a solution of 16.5 g (0.06 m) of N-carbomethoxymethyl-L-proline benzyl ester [R. Adams, J. Am. Chem. Soc. 81 5803 (1959)] and 50 ml of ethanol. After shaking under hydrogen on a low pressure hydrogenation apparatus for 2 hours, the mixture was filtered. The filtrate was evaporated. After ethanol was added and evaporated, the syrupy residue was dissolved in 1:1 toluene-ether and acidified with cold ethereal hydrogen chloride. The white solid resulting was separated and washed with ether to give 13.8 g of crude N-carbomethoxymethyl-L-proline hydrochloride, m.p. 191°-193°.

A mixture of 2.23 g (0.01 m) of N-carbomethoxymethyl-L-proline hydrochloride, 3.13 g (0.01 mole) of L-alanyl-L-proline, benzyl ester hydrochloride, 2.70 g (0.02 m) of 1-hydroxybenzotriazole, 2.3 g (0.02 m) of N-ethylmorpholine and 40 ml of dry tetrahydrofuran was cooled in ice/water, then, reacted with 2.06 (0.01 m) of dicyclohexylcarbodiimide at room temperature for 17 hours. The solids were separated by filtration. The filtrate was diluted with ethyl acetate and washed 3 times with 50 ml of 1.5% acetic acid, water, 5% sodium bicarbonate solution and brine. The dried organic layer was evaporated to give 4.3 g of a yellow syrup. The syrup was taken over a silica gel column and eluted with methylene chloride, 1% methanol/methylene chloride and 1½% methanol/methylene chloride to give 2.1 g (47%) of N-carbomethoxymethyl-L-prolyl-L-alanyl-proline, benzyl ester, a pro-drug of the desired end product.

This material, 2.1 g, in 30 ml of methanol was added to a mixture of 5.0 g of barium hydroxide hydrate in 40 ml of water. After stirring for 4 hours, carbon dioxide gas was passed through the mixture to precipitate barium carbonate. The colorless filtrate was evaporated to give a white solid, 1.25 g (78%), as the desired tripeptide product.

A sample (300 mg) was recrystallized from methanol-/ethyl acetate to give a white solid, m.p. 270° (dec.) which is the barium salt.

The unpurified solid (0.9 g) was dissolved in water. The mixture was filtered. The filtrate was adjusted to 3.5 pH with dilute sulfuric acid. The barium sulfate was separated by filtration. The filtrate was evaporated to give N-carboxymethyl-L-prolyl-L-alanyl-L-proline sulfate, 190°–196° (dec.).

Anal. Calcd. for $C_{15}H_{23}N_3O_6 \cdot \frac{1}{2}H_2SO_4 \cdot \frac{1}{2}H_2O$: C, 48.06; H, 6.59; N, 11.20. Found: C, 48.48, 48.21; H, 6.69, 6.78; N, 10.80, 10.74 $[\alpha]_D^{25} = (C, 1, 1:1\ CH_3OH \cdot H_2O)\ -132.2°$.

In the renal vasodilator activity test in 3 anesthetized dogs, the barium salt gave a 21.7% increase in renal blood flow and 15% decrease in renal vascular resistance at 30 μg/kg/min.

EXAMPLE 2

A mixture of 6.0 g (0.025 m) of the benzyl ester of L-proline hydrochloride, 6.75 g (0.05 m) of 1-hydroxybenzotriazole, 3.2 ml (0.025 m) of N-ethylmorpholine, 6.63 g (0.025 m) of L-tert.-butoxycarbonylphenylalanine, 5.15 g (0.025 m) of dicyclohexylcarbodiimide and 35 ml of dry tetrahydrofuran was stirred at 0° briefly, then, at 25° for 4 hours. The mother liquor was separated and evaporated. The residue was dissolved in ethyl acetate and dilute hydrochloric acid. The layers separated. The aqueous layer was extracted with ethyl acetate. The combined organic layers were washed with dilute hydrochloric acid, water, 5% sodium bicarbonate solution and brine. The organic layer was dried and evaporated to give 10.3 g (91%) of N-tert.-butoxycarbonyl-L-phenylalanyl-L-proline, benzyl ester.

This material (7.0 g) was reacted with a solution of 10 ml of trifluoroacetic acid, 40 ml of dry methylene chloride and 4 ml of 1,3-dimethoxybenzene at 25° for 2 hours. Working up as described above gave 5.57 g of L-phenylalanyl-L-proline, benzyl ester, hydrochloride.

The benzyl ester (2.23 g, 0.01 m) was reacted with 3.89 g of N-carbomethoxymethyl-L-proline hydrochloride, 2.70 g (0.02 m) of 1-hydroxybenzotriazole, 4.0 ml of N-ethylmorpholine, 2.06 g (0.01 m) of dicyclohexylcarbodiimide and 40 ml of dry tetrahydrofuran at 25° for 17 hours, as described above, to give 2.9 g of N-carbomethoxymethyl-L-prolyl-L-phenylalanyl-L-proline, benzyl ester, purified over silica gel.

This diester pro-drug (1.1 g, 2.1 mm) was dissolved in 30 ml of methanol and reacted with a warm solution of 5.0 g of barium hydroxide in 40 ml of water. The mixture was stirred at 25° for 4 hours, then, excess carbon dioxide was added. The barium carbonate was removed by filtration using a filter aid. The filtrate was evaporated and the residue azeotroped with ethanol to give, as described above, 0.72 g (82%) of the barium salt and, then, 0.89 g of the hemisulfate salt of N-carboxymethyl-L-prolyl-L-phenylalanyl-L-proline, m.p. 145°–148°.

Anal. Calcd. for $C_{21}H_{25}N_3O_6 \cdot \frac{1}{2} \cdot Ba \cdot H_2O$: C, 51.15; H, 5.31; N, 8.52; Ba, 13.92. Found: C, 51.47, 51.64; H, 5.27, 5.50; N, 5.28, 5.28; Ba 12.60 $[\alpha]_D^{25} = (C, 1, H_2O)\ -43.9°$.

Anal. Calcd. for $C_{21}H_{27}N_3O_6 \cdot \frac{1}{2}H_2SO_4$: C, 54.07, H, 6.04, N, 9.01. Found: C, 53.71, 53.64, H, 5.90, 5.94; N, 8.82, 8.91.

This sulfate increased renal blood flow at 30 and 300 μg/kg/min. The barium salt was not active within the parameters of anesthetized dog screening test.

EXAMPLE 3

Using the methods described above, 7.6 g of N-tert.-butoxycarbonyl-β-alanyl-L-proline, benzyl ester was prepared by the described acylation using dicyclohexylcarbodiimide. The protective group was removed by using trifluoroacetic acid to give β-alanyl-L-proline, benzyl ester hydrochloride. This compound (6.39 g, 0.02 m) was condensed with 2.23 g (0.01 m) of N-carbomethoxymethylproline hydrochloride by reacting in the presence of 2.7 g (0.02 m) of 1-hydroxybenzotriazole, 12 ml of N-ethylmorpholine, 2.06 g (0.01 m) of dicyclohexylcarbodiimide in 50 ml of dry tetrahydrofuran at room temperature for 17 hours. The product was 1.9 g of syrupy N-carbomethoxymethyl-L-prolyl-β-alanyl-L-proline, benzyl ester, the pro-drug precursor of the desired diacid.

The diester (1.75 g, 3.9 mm) was hydrolyzed using barium hydroxide and methanol, then, treated with sulfuric acid to give 1.2 g of a white solid, N-carboxymethyl-L-prolyl-β-alanyl-L-proline sulfate.

Anal. Calcd. for $C_{15}H_{23}N_3O_6 \cdot \frac{1}{2}H_2SO_4$: C, 46.15; H, 6.20; N, 10.76. Found: C, 45.81; 46.14; H, 6.50, 6.52; N, 9.94, 10.22; $[\alpha]_D^{25} = (0.8, H_2O)\ -70.4°$.

In the spontaneously hypertensive rat test (n=3) at 25 mg/kg i.p., the compound gave the following results in the diuretic naturetic assay: $Na^{\ominus}$ 676.04 (control 126.76); $K^{\ominus}$ 242.53 (85.12); Urine, ml/rat, 16(3). It also increased renal blood flow and decreased renal vascular resistance in two anesthetized dogs at 3, 30 and 300 μg/kg/min. In a secondary test in three dogs, this compound had an $ED_{15}$ of 12 μg/kg compared to 3.5 μg/kg for dopamine (i.v.).

EXAMPLE 4

Using the same reactions described above, 7.23 g (0.03) of ethyl β-bromopropionate and 7.33 g (0.04 m) of proline benzyl ester hydrochloride gave N-(2-carbethoxy)ethyl-L-proline, benzyl ester (4.6 g, 50.2%). This compound (4.6 g, 0.015 m) was hydrogenated over palladium-on-carbon to give 2.96 g (78%) of N-(2-carbethoxy)ethyl-L-propline, hydrochloride, m.p. 169°–171°. This compound (2.42 g, 0.0096 m) was condensed with 2.25 g (0.0072 m) of L-alanyl-L-proline, benzyl ester hydrochloride in the dicyclohexylcarbodiimide procedure to give 0.8 g of N-(2-carbethoxy)ethyl-L-prolyl-L-alanyl-L-proline, benzyl ester. The pro-drug precursor was hydrolyzed with barium hydroxide in aqueous methanol to give 0.498 g (64%) of N-(2-carboxyethyl)-L-prolyl-L-alanyl-L-proline, m.p. 133°–136°.

Anal. Calcd. for $C_{16}H_{25}N_3O_6 \cdot C_2H_5OH\ 1H_2O$; C, 51.54; H, 7.93; N, 10.02. Found: C, 51.95, 51.72; H, 7.12, 7.32; N, 10.19, 10.04. $[\alpha]_D^{25} = (1, H_2O)\ -147.3°$.

This compound in 2 anesthetized dogs demonstrated an accumulative effect at 300 μg/kg/min dose of 34% increase in renal blood flow and 23% decrease in renal vascular resistance.

EXAMPLE 5

D,L-β-Methyl-β-alanyl-L-proline, benzyl ester hydrochloride (5.95 g, 0.017 m, prepared as described in Example 1) was reacted with 4.41 g (0.015 m) of L-N-[5-(carbomethoxy)pentyl]proline, hydrochloride, which had been prepared by reacting ethyl-6-bromocaproate with proline, benzyl ester hydrochloride followed by catalytic hydrogenation to split the benzyl ester. The condensing agent was dicyclohexylcarbodiimide in the presence of 1-hydroxybenzotriazole and N-ethylmorpholine in tetrahydrofuran. The product was 1.5 g of syrupy N-5-carboethoxypentamethylenyl)-L-prolyl-D,L-β-methyl-β-alanyl-L-proline, benzyl ester, m/e at 530 is M+1. Barium hydroxide hydrolysis of 0.5 g of the ester gave 0.2 g of the desired L-(N-5-carboxypentamethylenyl)prolyl-D,L-$\beta$-methyl-$\beta$-alanyl-L-proline, m.p. 80°–84°; $[\alpha]_D^{25}$=(C,1, 1:1 methanol/water) −90.1°.

Anal. Calcd. for $C_{20}H_{33}N_3O_6 1.25H_2O$: C, 55.35; H, 8.36; N, 9.68. Found: C, 55.49; H, 8.78; N, 9.05.

EXAMPLE 6

Using the same methods described above, 12.5 g (0.76 m) of D,L-3-amino-3-phenylpropionic acid was reacted with 9.6 g (0.095 m) of triethylamine and 20.7 g (0.095 m) of di-tert.-butyldicarbonate in 250 ml of dimethylformamide at 25° for 17 hours to give 19.9 g (79%) of the white solid t-boc derivative, m.p. 115°–117°. This material, 7.95 g (0.03 m) was condensed with 7.23 g (0.05 m) of L-proline, benzyl ester hydrochloride to give 13.6 g of the dipeptide. The protective group was removed by treatment with trifluoroacetic acid in methylene dichloride and 1,3-dimethoxybenzene to give, after anhydrous hydrogen chloride treatment, D,L-$\beta$-phenyl-$\beta$-alanyl-L-proline, benzyl ester, hydrochloride as a white solid. This material (10.1 g, 0.026 m) was condensed with 5.81 g (0.026 m) of L-N-carbomethoxymethylproline hydrochloride to give, after chromatography over silica gel with a methanol in methylene chloride gradient, 1.8 g of N-carbomethoxymethyl-L-prolyl-D,L-$\beta$-phenyl-$\beta$-alanyl-L-proline, benzyl ester. Hydrolysis of the diester with barium hydroxide followed by acidification with dilute sulfuric acid gave 0.99 of N-carboxymethyl-L-prolyl-D,L-$\beta$-phenyl-$\beta$-alanyl-L-proline, sulfate, m.p. 256°–260°, $[\alpha]_D^{25}$=(C,1, 1:1 methanol/water) −43.2°.

Anal. Calcd. for $C_{21}H_{27}N_3O_6.0.25H_2SO_4.H_2O$: C, 54.83; H, 6.46; N, 9.13. Found: C, 54.86; H, 6.43; N, 8.24.

EXAMPLE 7

Using the same reactions described above 12.5 g (0.12 m) of D,L-$\beta$-methyl-$\beta$-alanine (D,L-3-aminobutyric acid) was reacted with 12.12 g (0.15 m) of triethylamine and 32.7 (0.15 m) of di-tert.butyldicarbonate in 300 ml of dimethylformamide to give 18.5 g (76%) of the white solid t-boc., m.p. 90°–92°. This material (4.06 g, 0.02 m) was condensed with 4.82 g (0.02 m) of proline, benzyl ester hydrochloride using the dicyclohexylcarbodiimide reaction described above, at 25° for 17 hours, to give, after trifluoroacetic acid and anhydrous hydrogen chloride treatment, D,L-$\beta$-methyl-$\beta$-alanyl-L-proline, benzyl ester, hydrochloride. This material (3.5 g, 0.01 m) was condensed with 1.12 g (0.005 m) of N-carbomethoxymethylproline hydrochloride, as discussed above, to give N-carbomethoxymethyl-L-prolyl-D,L-$\beta$-methyl-$\beta$-alanyl-L-proline, benzyl ester. Barium hydroxide hydrolysis, then, sulfuric acid salt formation gave N-carboxymethyl-L-prolyl-D,L-$\beta$-methyl-$\beta$-alanyl-L-proline hemisulfate, m.p. 135° $[\alpha]_D^{25}$= −63.3° (C,1, 50% aqueous methanol).

The diastereoisomeric mixture (S, S, S and S, R, S) was separated by application of the mixture in 9:1 water-methanol to a C-~reverse phase high pressure liquid chromatographic column using 90:10:0.1 of water-methanol-trifluoroacetic acid as the eluent. Base line separation ($\alpha$=1.29) allowed the separation of the S, S, S and S, R,S-isomers with optical rotations of $[\alpha]_D^{25}$= −59.9° (C,1, 1:1 $CH_3OH.H_2O$) and $[\alpha]_D^{25}$= −44.8° (C,1, 1:1 $CH_3OH.H_2O$), respectively.

Substituting N-(2-carbethoxy)ethyl-L-proline, hydrochloride for its lower homologue in this procedure gives N-(2-carboxy)ethyl-L-prolyl-D,L-$\beta$-methyl-$\beta$-alanyl-L-proline. Substituting N-(3-carbomethoxy)propyl-D,L-proline, hydrochloride (prepared as described in Example 4) into the procedure of Example 4 in place of N-(2-carbethoxy)ethyl-L-proline hydrochloride gives N-carboxypropyl-D,L-prolyl-L-alanyl-L-proline as the base.

EXAMPLE 8

A mixture of 10.0 g (0.0529 m) of N-tert.-butoxycarbonyl-D-alanine, 12.75 g (0.0529 m) of L-proline, benzyl ester hydrochloride, 14.28 g (0.0106 m) of 1-hydroxybenzotriazole, 15 ml of N-methylmorpholine and 125 ml of dry tetrahydrofuran together with 10.9 g (0.0529 m) of dicyclohexylcarbodiimide and 15 ml of dry dimethylformamide, reacted and worked up as described above, gave 20.4 g of crude N-tert.-butoxycarbonyl-D-alanyl-L-proline benzyl ester. Removal of the t-boc protective group, as described, gave D-alanyl-L-proline, benzyl ester hydrochloride, m.p. 140°–142°. This material (8.3 g, 0.0265 m) was condensed with 5.92 g (0.0265 m) of N-carbomethoxymethyl-L-prolinehydrochloride as described, to give 3.1 g of syrupy N-carbomethoxyethyl-L-prolyl-D-alanyl-L-proline, benzyl ester. Barium hydroxide treatment of 3.0 g (6.7 mm) of the above diester gave 2.1 g of N-carboxymethyl-L-prolyl-D-alanyl-L-proline; m.p. 145°–148° $[\alpha]_D^{25}$= −39.9° (C,1, 1:1 $CH_3OH.H_2O$).

Similarly N-2-carboxyethyl-L-prolyl-D-alanyl-L-proline was prepared; m.p. 170° d. (softening at 142°–145°) $[\alpha]_D^{25}$= −67.9° (C,1, 1:1 $CH_3OH.H_2O$).

EXAMPLE 9

A mixture of 6.28 g (0.0332 m) of N-tert.-butoxycarbonyl-$\beta$-alanine, 5.0 g (0.0332 m) of L-proline amide hydrochloride, 8.96 g (0.0664 m) of 1-hydroxybenzotriazole, 12 ml of N-methylmorpholine, 75 ml of tetrahydrofuran, 40 ml of dimethylformamide and 6.84 g (0.0332 m) of dicyclohexylcarbodiimide was stirred at 25° for 17 hours. The solvents were evaporated in vacuo and the residue dissolved in ethyl acetate and water. The separated organic layer was washed with small volumes of dilute hydrochloric acid, brine, 5% bicarbonate and brine. The dried extract was concentrated to give 3.2 g of syrupy N-tert.-butoxycarbonyl-$\beta$-alanyl-L-proline amide. The methane chemical ionization mass spectrum was in agreement with the dipeptide structure.

This product was dissolved in 35 ml of dry methylene dichloride, cooled in ice water and 15 ml of trifluoroacetic acid was added. The solution was stirred at 0° for 15 minutes and at 25° for 3 hours. The solvents were evaporated in vacuo at 40° to give the syrupy trifluoroacetate salt of $\beta$-alanyl-L-proline amide. This compound (~0.01 m) was condensed with N-carbomethoxymethyl-L-proline hydrochloride, as described, to give N-carbomethoxymethyl-L-prolyl-$\beta$-alanyl-L-proline amide. Barium hydroxide treatment gave N-carboxymethyl-L-prolyl-$\beta$-alanyl-L-proline amide.

EXAMPLE 10

Substituting N-carbomethoxymethyl-L-dehydroproline, benzyl ester, prepared by the Adams alkylation method, for the N-carbomethoxymethyl-L-proline ester in Example 1 gives N-carboxymethyl-L-dehydroprolyl-L-alanyl-L-proline as the sulfate salt. Substituting in Example 1 N-carbomethoxymethyl-pyroglutamic acid, benzyl ester, prepared by the Adams alkylation method, gives N-carboxymethylpyroglutamyl-L-alanyl-L-proline. Substituting in Example 1 2-pyrrolidinylacetic acid, benzyl ester, for the benzyl ester of L-proline gives N-carboxymethyl-L-prolyl-L-alanyl-2-pyrrolidinylacetic acid. Substituting the t-boc derivative of β-(2-thienyl)alanine (The Chemistry of Heterocyclic Compound Volume III, Hartough, page 262) for the alanine derivative of Example 1 gives N-carboxymethyl-L-prolyl-D,L-β-(2-thienyl)-alanyl-L-proline. Substituting N-methylsulfomethylproline benzyl ester, prepared using the known methyl ester of chloromethanesulfonic acid in the Adams alkylation process, in Example 1 gives N-sulfomethyl-L-prolyl-L-alanyl-L-proline. Using the known dimethyl ester of chloromethylphosphonic acid in the Adams alkylation and, then, substituting N-dimethylphosphonomethyl proline benzyl ester in Example 1 gives N-phosphonomethyl-L-prolyl-L-alanyl-L-proline.

What is claimed is:

1. A chemical compound of the structural formula:

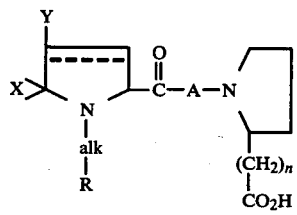

in which:
R is carboxy, sulfo or phosphono; alk is a straight or branched alkylene chain of 1–5 carbons which is not ethylidene;
X is O or H,H;
Y is H or, when X is H,H, OH;
is an optional carbon-carbon bond, when X is H,H and Y is H;
n is an integer of from 0–3 inclusive; and
A is an amino acid residue derived from D- or L-Ala, D- or L-Phe, D- or L-β-methyl-β-Ala, D- or L-phenyl-Gly, D- or L-β-phenyl-β-Ala, D- or L-β-thienyl-Gly, D- or L-β-Ala, γ-aminobutyric acid; D- or L-2-aminobutyric acid, D- or L-nor-Val, D- or L-Leu, 3-amino-3-methyl butyric acid, 2-methyl-Ala or a N-methyl derivative of said residues; or a pharmaceutically acceptable salt or prodrug derivative of said compound.

2. The compound of claim 1 in which the configuration of the amino acid units is L.

3. The compound of claim 2 in which R is carboxy, X is H,H, Y is hydrogen and n is O.

4. The compound of claim 3 in which A is a β-Ala.

5. The compound of claim 1 being N-(2-carboxymethyl)-L-prolyl-β-alanyl-L-proline of a pharmaceutically acceptable salt thereof.

6. The compound of claim 1 being N-(2-carboxymethyl)-L-prolyl-β-alanyl-L-proline.

7. The compound of claim 1 being N-(2-carboxyethyl)-L-prolyl-L-alanyl-L-proline or a pharmaceutically acceptable salt thereof.

8. The compound of claim 1 being N-carboxymethyl-L-prolyl-L-phenylalanyl-L-proline or a pharmaceutically acceptable salt thereof.

9. The compound of claim 1 being N-carboxymethyl-L-prolyl-D,L-β-methyl-β-alanyl-L-proline or a pharmaceutically acceptable salt thereof.

10. The compound of claim 1 being N-carboxymethyl-L-prolyl-D-β-methyl-β-alanyl-L-proline or a pharmaceutically acceptable salt thereof.

11. A pharmaceutical composition effective for improving kidney function comprising a nontoxic, therapeutically effective quantity of a compound of claims 1, 2, 3, 4, 5, 6, 7, 8 or 9 combined with a carrier therefor.

12. The method of improving kidney function in a subject in need thereof comprising administering orally or parenterally to said subject a nontoxic, therapeutically effective quantity of a compound of claims 1, 2, 3, 4, 5, 6, 7, 8 or 9.

* * * * *